(12) United States Patent
Ryu et al.

(10) Patent No.: US 9,090,763 B2
(45) Date of Patent: Jul. 28, 2015

(54) RESIN BLEND CAPABLE OF FORMING A LAYER-SEPARATED STRUCTURE AND METHOD OF MAKING LAYER-SEPARATED STRUCTURE THEREFROM

(71) Applicant: LG CHEM, LTD., Seoul (KR)

(72) Inventors: Jin Young Ryu, Daejeon (KR); Hak Shin Kim, Daejeon (KR); Houng Sik Yoo, Seoul (KR); Eun Joo Choi, Daejeon (KR); Young Jun Hong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 13/688,192

(22) Filed: Nov. 28, 2012

(65) Prior Publication Data

US 2013/0164535 A1     Jun. 27, 2013

Related U.S. Application Data

(63) Continuation-in-part of application No. PCT/KR2011/003882, filed on May 26, 2011.

(30) Foreign Application Priority Data

| May 28, 2010 | (KR) | 10-2010-0050639 |
| Oct. 14, 2010 | (KR) | 10-2010-0100385 |
| May 26, 2011 | (KR) | 10-2011-0050289 |
| May 26, 2011 | (KR) | 10-2011-0050298 |

(51) Int. Cl.
*B32B 5/16* (2006.01)
*B32B 7/00* (2006.01)
(Continued)

(52) U.S. Cl.
CPC ............... *C08L 27/12* (2013.01); *B32B 27/08* (2013.01); *C08J 3/126* (2013.01); *C08L 33/04* (2013.01);
(Continued)

(58) Field of Classification Search
CPC .... C08L 83/00; C08L 33/12; Y10T 428/2991; Y10T 428/2998
USPC ............... 428/403, 407, 212, 421, 423.1, 446
See application file for complete search history.

(56) References Cited

U.S. PATENT DOCUMENTS 4,159,288 A * 6/1979 Carson et al. ............... 525/228
6,818,173 B1 * 11/2004 Khait ............................ 264/540
(Continued)

FOREIGN PATENT DOCUMENTS

| JP | 2000-239532 | * | 9/2000 |
| JP | 2006306916 A | | 11/2006 |
| WO | 2008/019229 A2 | | 2/2008 |

OTHER PUBLICATIONS

International Search Report issued in Int'l Appln. No. PCT/KR2011/003882 dated Feb. 24, 2012, 2 pages.
(Continued)

*Primary Examiner* — Holly Le
(74) *Attorney, Agent, or Firm* — Rothwell, Figg, Ernst & Manbeck, P.C.

(57) ABSTRACT

Provided are a resin blend for forming a layer-separated structure, a pellet, a method of preparing a resin article using the same, and a resin article. The resin blend may include a first resin, and a second resin including a resin to which a fluorine or fluorine-substituted organic functional group is introduced and having a difference in surface energy from the first resin at 25° C. of 0.1 to 35 mN/m. The resin blend can improve mechanical and surface characteristics of a resin article. Also, the resin blend can realize excellent contamination resistance of a resin article. Further, since coating or plating is not required for manufacturing a resin article, a manufacturing time and/or cost can be reduced, and productivity can be increased.

16 Claims, 3 Drawing Sheets

(51) Int. Cl.
*B32B 27/36* (2006.01)
*B32B 27/38* (2006.01)
*C08L 27/12* (2006.01)
*C08L 33/12* (2006.01)
*B32B 27/08* (2006.01)
*C08L 33/04* (2006.01)
*C08L 101/00* (2006.01)
*C08J 3/12* (2006.01)
*C08L 101/04* (2006.01)
*G01N 21/3563* (2014.01)

(52) U.S. Cl.
CPC .............. C08L 33/12 (2013.01); C08L 101/00 (2013.01); C08L 101/04 (2013.01); *C08J 2400/102* (2013.01); *G01N 21/3563* (2013.01); *Y10T 428/2991* (2015.01); *Y10T 428/2998* (2015.01); *Y10T 428/3154* (2015.04)

(56) References Cited

U.S. PATENT DOCUMENTS

2003/0198769 A1* 10/2003 Jing et al. ............... 428/36.91
2011/0166294 A1* 7/2011 Brusson et al. ............ 525/174
2013/0157056 A1* 6/2013 Ryu et al. ................. 428/407
2014/0255700 A1* 9/2014 Choi et al. ................ 428/407
2015/0025171 A1* 1/2015 Yoo et al. ................. 522/112

OTHER PUBLICATIONS

M. Wei et al.: "Core-Sheath Structure in Electrospun Nanofibers from Polymer Blends," Macromolecular Materials and Engineering, vol. 291, pp. 1307-1314, 2006.
B.J. Keestra et al.: "Two Component Injection Molding of Phase Separating Blends," International Polymer Processing, vol. 21, pp. 168-174, 2006.
N. Zhao et al.: "A Novel Ultra-hydrophobic Surface: Statically Non-wetting but Dynamically Non-sliding," Advanced Functional Materials, vol. 17, pp. 2739-2745, 2007.
M. Schnell et al.: "Evolution of viscosities and morphology for the two-phase system polyethylene oxide/poly (dimethylsiloxane)," Chemistry and Materials Science, Theologica Acta, vol. 47, pp. 469-476, 2008.
Office Action issued in Chinese Patent Application No. 201180063946.7 on May 6, 2014 along with English translation, 18 pages.
Y. Kano et al.: "Surface segregation and miscibility in blends of poly(ethyl acrylate) with poly(vinylidene fluoride-co-hexafluoroacetone)", Int. J. Adhesion and Adhesives, vol. 15, No. 4, 1995, pp. 219-224.

* cited by examiner

RESIN BLEND CAPABLE OF FORMING A LAYER-SEPARATED STRUCTURE AND METHOD OF MAKING LAYER-SEPARATED STRUCTURE THEREFROM

CROSS-REFERENCE TO RELATED APPLICATION

This application is a continuation-in-part of International Application PCT/KR2011/003882, with an international filing date of May 26, 2011, which claims priority to and the benefit of Korean Patent Application No. 2010-0050639, filed May 28, 2010, Korean Patent Application No. 2010-0100385, filed Oct. 14, 2010, Korean Patent Application No. 2011-0050289, filed May 26, 2011, and Korean Patent Application No. 2011-0050298, filed May 26, 2011, the disclosures of which are incorporated herein by reference in their entireties.

BACKGROUND

Plastic resins have various applications including automobile parts, helmets, parts of electric devices, parts of textile spinning machines, toys or pipes because of their easy processability and excellent properties such as tensile strength, modulus of elasticity, heat resistance and impact resistance.

Particularly, home appliance functions as home interior accessories as well as its own function as home appliance and parts of automobiles and toys are in direct contact with a human body, these products are required to be environment-friendly and to have excellent scratch resistance. However, plastic resins are generally decomposed by oxygen in the air, ozone and light and easily changed in color when exposed to an external environment for over a certain period of time. As a result, plastic resins suffer from decrease of weather resistance and strength, which makes them to be easily broken. Thus, an additional coating or plating process has been usually applied to plastic resins to improve these problems and surface properties. In addition, thermal plastic resins are easily contaminated by dust, water or oil. Thus, in order to improve surface characteristics of the plastic resins, coating or plating with anti-contamination agent or UV coating has been suggested. However, such a coating or plating process can drop efficiency and economic feasibility of a manufacturing process of plastic resins or generate large amount of toxic materials during the process or disposal of a product.

Accordingly, various methods have been suggested to improve properties of plastic resins such as scratch resistance, heat resistance and weather resistance without using an additional coating or plating process. For example, a method of adding inorganic particles to high molecule resins has been suggested to improve physical properties such as abrasion resistance and stiffness of the resins. However, this method may deteriorate the processability of plastic resins and impact strength and gloss due to the addition of inorganic particles.

SUMMARY OF THE INVENTION

The present invention provides a resin blend for melt processing. The resin blend can improve mechanical and surface characteristics of a resin article by enabling formation of a surface layer on the resin article through a layer separation. Also, the resin blend can provide excellent contamination resistance to a resin article. Further, since a separate step for coating or plating is not required for manufacturing a resin article, a manufacturing time and/or manufacturing cost can be reduced, and productivity can be increased.

The present invention further provides a pellet produced by using the resin blend.

The present invention still further provides a method of preparing a resin article by using the resin blend or the pellet.

The present invention still further provides a resin article produced by the resin blend that has improved surface characteristics such as anti-contamination function.

In one embodiment, a resin blend includes a first resin and a second resin including a resin to which a fluorine or fluorine-substituted organic functional group is introduced and having a difference in surface energy from the first resin at 25° C. of 0.1 to 35 mN/m.

In another embodiment, a pellet includes a core including a first resin and a shell including a second resin including a resin to which a fluorine or fluorine-substituted organic functional group is introduced and having a difference in surface energy from the first resin at 25° C. of 0.1 to 35 mN/m.

In another embodiment, a method of preparing a resin article includes melting the resin blend to form a melt blend and processing the melt blend to form the resin article. The second resin includes a resin to which a fluorine or fluorine-substituted organic functional group is introduced. A surface energy difference between the first resin and the second resin is 0.1 to 35 mN/m at 25° C.

In another embodiment, a method of preparing a resin article includes melting a pellet including a core including a first resin and a shell including a second resin to form a melt, and processing the melt to form the resin article. The second resin includes a resin to which a fluorine or fluorine-substituted organic functional group is introduced. A surface energy difference between the first and second resins is 0.1 to 35 mN/m at 25° C.

In another embodiment, a resin blend for forming a layer-separated structure includes a first resin and a second resin having a lower surface energy than the first resin. The second resin includes a resin to which a fluorine or fluorine-substituted organic functional group is introduced. Also, the second resin is disposed between the first resin and an ambient air in response to a melting process.

In another embodiment, a resin blend for forming a layer-separated structure includes a base resin and a functional resin. The functional resin includes a resin to which a fluorine or fluorine-substituted organic functional group is introduced. Also, a value of a surface energy of the functional resin is different from that of the base resin, and the value of the surface energy of the functional resin is dependent on the properties of the base resin.

In another embodiment, a resin article produced by melt processing includes a first resin layer; a second resin layer formed on the first resin layer; and an interface layer formed between the first resin layer and the second resin layer. Here, the interface layer includes a first resin and a second resin. Also, the second resin layer includes a resin to which a fluorine or fluorine-substituted organic functional group is introduced.

In another embodiment, a resin article produced by melt processing that includes a first resin layer; and a second resin layer formed on the first resin layer. Here, the component of the first resin layer is detected on a surface of the second resin layer by an infrared (IR) spectrometer. Also, the second resin layer includes a resin to which a fluorine or fluorine-substituted organic functional group is introduced.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EMBODIMENTS

Figure 1:
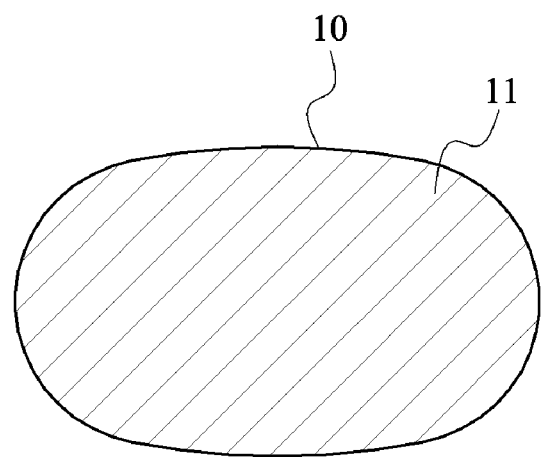
FIG. 1 is an illustrative schematic diagram showing a resin blend, according to one embodiment of the present invention.
Figure 2:
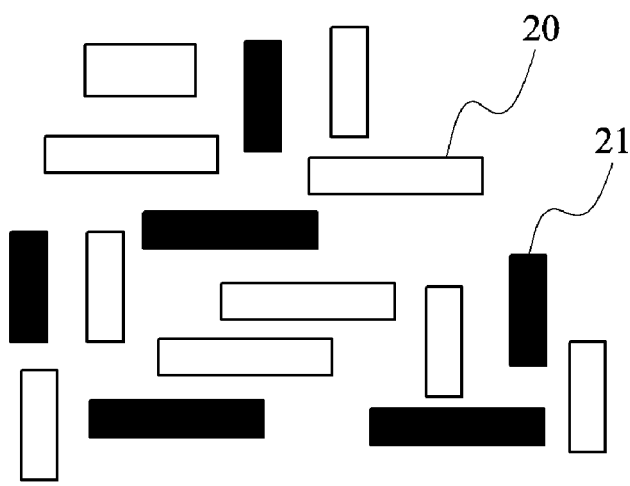
FIG. 2 is an illustrative schematic diagram showing a resin blend, according to another embodiment of the present invention.

Hereinafter, a resin blend for preparing a resin article having a surface layer formed as a result of a layer separation without a separate coating or plating process, a pellet and a method of preparing a resin article using the same according to embodiments of the present invention will be described in detail.

A "blend" may be a mixture of two or more different species of resins. A type of blend may include, but is not limited, a mixture of two or more resins in one matrix, or a mixture of two or more kinds of pellets. Particularly, the mixture of two or more resins in one matrix may be a pellet containing a mixture of two or more resins. For example, a mixture of a first resin and a second resin can be contained in a single pellet. Alternatively, in the mixture of two or more kinds of pellets, each kind of pellet contains one kind of resin. For example, a blend can include a mixture of a pellet containing a first resin and a pellet containing a second resin A "melting process" or "melt processing" may refer to a process of melting the resin blend at not less than a melting temperature (Tm) of the resin blend to form a melt blend and forming a desired product by using the melt blend. For example, the melting process or melt process may include injection molding, extrusion, blow molding, expanding molding and the like.

A "layer separation" may indicate that a portion of a resin blend that is separated from the remaining resin blend by phase-separation, forms a layer that is visibly separated from a layer of the remaining resin blend. For example, the separated portion of the resin blend can be rich with or contain a substantial amount of a second resin and the remaining resin blend can be rich with or contain a substantial amount of a first resin. The layer separation results in a layer-separated structure in a resin article or a pellet, which is distinguished from a sea-island structure where the phase-separated portion is partially distributed in the entire resin blend. The layer separation of the resin blend results in two or more separate layers, preferably two separate layers formed in a resin article or a pellet prepared by the resin blend.

The present inventors confirmed through experimentation that a layer separation occurs when a resin blend comprising a first resin and a second resin having contamination resistance and certain physical properties different from the first resin is used, and that such a layer separation enables to obtain substantially the same effects as applying a coating on a surface of pellets or resin articles in melting process or melt processing. Through such a layer separation, the second resin forms a surface layer on the pellets or the resin articles.

Thus, the resin blend for a melting process or melt processing according to one embodiment of the present invention may provide a resin article having improved mechanical and surface characteristics such as contamination resistance with a reduced manufacturing cost and time without the need of an additional processing such as coating or plating. For example, the resin blend of the present invention may be layer-separated by a melting process to form a resin article having a specific function on a surface of the resin article, without an additional process, such as coating and plating.

The layer separation may be attributed to a difference in physical properties between a first and second resins and/or a molecular weight distribution of the second resin. Here, the different physical properties may, for example, include surface energy, melt viscosity and a solubility parameter. Although it is illustrated here that two resins are blended for the purpose of explanation of the present invention, it will be apparent to one of skilled in the art that three or more resins having different physical properties may be blended and separated during melt processing.

In one embodiment, a resin blend for melt processing comprises a first resin and a second resin including a resin to which a fluorine or fluorine-substituted organic functional group is introduced and having a difference in surface energy from the first resin at 25° C. of 0.1 to 35 mN/m.

The difference in surface energy between the first and second resins at 25° C. may be 0.1 to 35 mN/m, 1 to 30 mN/m, or 1 to 20 mN/m. The difference in surface energy between the first and second resins at 25° C. can also be 1 to 10 mN/m, 0.5 to 10 mN/m, 5 to 35, 15 to 35 mN/m or 5 to 30 mN/m. It will be apparent to one of skilled in the art that the listed ranges are only examples for the purpose of the description of the present invention and any values within 0.1 to 35 mN/m can be chosen. The difference in surface energy between the first and second resins at 25° C. may be 0.1 to 35 mN/m, 1 to 30 mN/m, 1 to 20 mN/m, 1 to 10 mN/m, 0.5 to 10 mN/m, 5 to 35, 15 to 35 mN/m or 5 to 30 mN/m. It will be apparent to one of skilled in the art that the listed ranges are only examples for the purpose of the description of the present invention and any values within 0.1 to 35 mN/m can be chosen. By way of an example, in the case that the resin blend of the first and second resins is melt-processed such as extrusion or injection, the melt-processed resin blend is exposed to an ambient air. In the melt-processed resin blend, the first and second resins can be separated due to the higher affinity of the second resin to the ambient air compared to the first resin. Particularly, the second resin having a smaller surface energy compared to the first resin may have a hydrophobic property, and due to its fluidity in the melt-processed resin blend, move to surface that contacts the ambient air. Thus, the second resin may be positioned adjacent to an ambient air to form a second resin layer as a surface layer. A first resin layer may be positioned on an inner side of the second layer. Accordingly, a layer separation can occur between the first and second resins of the resin blend. When the difference in surface energy is too low such as less than 0.1 mN/m, the layer separation of the melt-processed resin blend does not easily occur and the second resin in a mixture of melting state can be difficult to be positioned on the surface by moving through the matrix of the resin blend. When the difference in surface energy is too high such as greater than 35 mN/m, the first and second resins may not be attached to each other due to a high difference of surface energy, and thus may be detached.

The lower and/or upper limits of the difference in surface energy may be any numeric value of 0.1 to 35 mN/m, and be dependent on the properties of the first resin. Particularly, when a first resin is used as a base resin and a second resin is used a functional resin to improve surface properties of a first resin, the second resin may be selected such that a difference in surface energy between the first and second resins is 0.1 to 35 mN/m at 25° C. Since a value of the surface energy of the second resin (e.g., functional resin) may be different based on the properties of the first resin (e.g., base resin), the difference in surface energy may be determined based on the properties of the first resin. The properties of the first resin may include, but is not limited to, a kind of the first resin, or a value of the surface energy of the first resin. In one embodiment, the difference in surface energy may be selected by considering hydrophobicity of the second resin in a melting mixture of the first and second resins.

Figure 3:
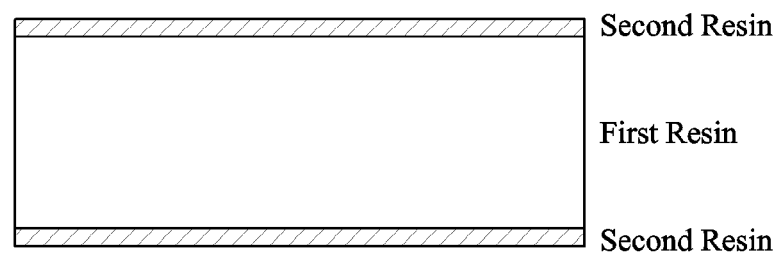
FIG. 3 is an illustrative schematic diagram showing a resin article formed by using a resin blend including a first resin and a second resin, according to one embodiment of the present invention.
Figure 4:
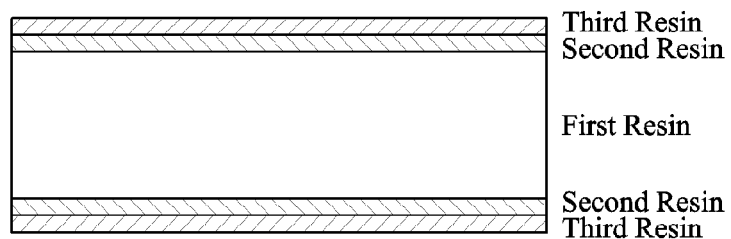
FIG. 4 is an illustrative schematic diagram showing a resin article formed by using a resin blend including a first resin, a second resin and a third resin, according to another embodiment of the present invention.
Figure 5:
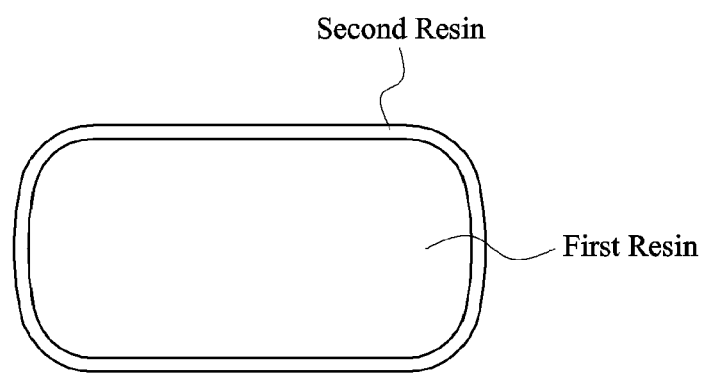
FIG. 5 is an illustrative schematic diagram showing a resin article, according to another embodiment of the present invention.

The resin blend may be separated into two or more layers. The resin blend including the first resin and the second resin may be layer-separated into three layers, i.e., Second resin layer/First resin layer/Second resin layer, as shown in FIG. 3, when two opposite sides of the melt-processed resin blend are exposed to the ambient air. Alternatively, when only one side of the melt-processed resin blend is exposed to the ambient air, the resin blend may be layer-separated into two layers, i.e., Second resin layer/First resin layer. Further, when a resin blend including a first resin, a second resin and a third resin is melt-processed, the melt-processed resin blend may be layer-separated into five layers, i.e., Third resin layer/Second resin layer/First resin layer/Second resin layer/Third resin layer, as shown in FIG. 4, by using the differences in surface energy among the three resins. Furthermore, when all sides of the melt-processed resin blend are exposed to the ambient air, the resin blend may be layer-separated into all direction to form a core-shell structure, as shown FIG. 5.

In another embodiment, a resin blend for a melt processing includes a first resin and a second resin including a resin to which a fluorine or fluorine-substituted organic functional group is introduced and having a difference in melt viscosity from the first resin of 0.1 to 3000 pa*s at a shear rate of 100 to 1000 s$^{-1}$ and at a processing temperature of the resin blend.

The difference in a melt viscosity between the first resin and the second resin may be 0.1 to 3000 pa*s, 1 to 2000 pa*s, or 1 to 1000 pa*s at a shear rate of 100 to 1000 s$^{-1}$ and at a processing temperature of the resin blend. The difference in a melt viscosity between the first resin and the second resin can also be 100 to 500 pa*s, 500 to 3000 pa*s, 1500 to 3000 pa*s, or 500 to 2500 pa*s at a shear rate of 100 to 1000 s$^{-1}$ and at a processing temperature of the resin blend. It will be apparent to one of skilled in the art that the listed ranges are only examples for the purpose of description of the present invention and any value within the range of 0.1 to 3000 pa*s at the above shear rate and at a processing temperature of the resin blend can be selected. When the difference in the melt viscosity is too low for example less than 0.1 pa*s at the shear rate and at a processing temperature of the resin blend, the layer separation of the melt-processed resin blend does not easily occur because the first and second resins are too easily mixed together. When the difference in the melt viscosity is too high for example greater than 3000 pa*s at the shear rate and at a processing temperature of the resin blend, the first and second resins may not be attached to each other due to a high difference of the melt viscosity and thus may be detached.

The lower and/or upper limits of the difference in melt viscosity may be any numeric value of 0.1 to 3000 pa*s, and be dependent on the properties of the first resin. Particularly, when a first resin is used as a base resin and a second resin is used as functional resin to improve surface properties of the first resin, the second resin may be chosen such that a difference in a melt viscosity between the first and second resins is 0.1 to 3000 pa*s at a shear rate of 100 to 1000 s$^{-1}$ and at a processing temperature of the resin blend. Since a value of the melt viscosity of the second resin (e.g., functional resin) may be different based on the properties of the first resin (e.g., base resin), the difference in the melt viscosity may be determined based on the properties of the first resin. The properties of the first resin may include, but is not limited to, a kind of the first resin, or a value of the melt viscosity of the first resin. In one embodiment, the difference in melt viscosity may be selected by considering fluidity of the second resin in a melt-processed blend of the first and second resins.

By way of an example, in the case that the resin blend of the first and second resins having the difference in melt viscosity of 0.1 to 3000 pa*s at a shear rate of 100 to 1000 s$^{-1}$ and at a processing temperature of the resin blend is used, when the resin blend of the first and second resins is melt-processed, the melt-processed resin blend is exposed to an ambient air. In the melt-processed resin blend, the first and second resins can be separated due to the difference of fluidity between the first resin and second resin. Particularly, the second resin having a smaller melt viscosity compared to the first resin may have a higher fluidity than the first resin, and move to a surface that contacts the ambient air. Thus, the second resin may be positioned adjacent to an ambient air to form a second resin layer as a surface layer. A first resin layer may be positioned on an inner side of the second layer. Accordingly, a layer separation can occur between the first and second resins of the resin blend.

The melt viscosity may be measured using a capillary flow meter, and indicates a shear viscosity (pa*s) at a predetermined processing temperature and shear rate (/s). The shear rate is a shear rate applied when the resin blend is processed, and may be selected depending on a processing method, for example, shear rate of 100 to 1000 s$^{-1}$. It will be apparent to one of skilled in the art to control the shear rate according to the processing method.

The processing temperature is a temperature at which the resin blend is processed. For example, when the resin blend is subject to a melt processing such as extrusion or injection, the processing temperature is a temperature at which the melt processing such as extrusion or injection is performed. The processing temperature may be controlled according to a resin subjected to melting processes such as extrusion or injection. It will be apparent to one of skilled in the art to control the processing temperature according to the kinds of resins of the resin blend. For example, a temperature for extruding or injecting a resin blend including a first a an ABS resin as a first resin and a second resin obtained by polymerizing a methyl methacrylate-based monomer may be 210 to 240° C.

In still another embodiment, a resin blend for melt processing includes a first resin and a second resin including a resin to which a fluorine or fluorine-substituted organic functional group is introduced and having a difference in solubility parameter from the first resin at 25° C. of 0.001 to 10 $(J/cm^3)^{1/2}$.

The difference in a solubility parameter between the first resin and the second resin at 25° C. may be 0.001 to 10 $(J/cm^3)^{1/2}$, 0.01 to 5 $(J/cm^3)^{1/2}$, or 0.01 to 3 $(J/cm^3)^{1/2}$. The difference in a solubility parameter between the first resin and the second resin at 25° C. can also be 0.01 to 2 $(J/cm^3)^{1/2}$, 0.1 to 1 $(J/cm^3)^{1/2}$, 0.1 to 10 $(J/cm^3)^{1/2}$, 3 to 10 $(J/cm^3)^{1/2}$, 5 to 10 $(J/cm^3)^{1/2}$, or 3 to 8 $(J/cm^3)^{1/2}$. The lower and/or upper limit of the difference in solubility parameter may be any numeric value of 0.001 to 10 $(J/cm^3)^{1/2}$, and be dependent on a solubility parameter of the first resin. It will be apparent to one of skilled in the art that the listed values are only examples for the purpose of description of the present invention and any value within the range of 0.001 to 10 $(J/cm^3)^{1/2}$ at 25° C. can be chosen. A solubility parameter is an intrinsic property of resin reflecting solubility depending on a polarity of each resin molecule, and the solubility parameter for each resin is generally known. When the difference in the solubility parameter is too small, for example, less than 0.001 $(J/cm^3)^{1/2}$, the layer separation does not easily occur because the first and second resins are too easily mixed together. When the difference in the solubility parameter is too big, for example, greater than 10 $(J/cm^3)^{1/2}$, the first and second resins may not be attached to each other due to a high difference of solubility parameter, and thus may be detached.

The lower and/or upper limits of the difference in solubility parameter may be any numeric value of 0.001 to 10 $(J/cm^3)^{1/2}$, and be dependent on the properties of the first resin. Particularly, when a first and second resins are used as a base and functional resins, respectively, the second resin may be chosen such that a difference in a solubility parameter between the first and second resins is 0.001 to 10 $(J/cm^3)^{1/2}$ at 25° C. Since a value of the solubility parameter of the second resin (e.g., functional resin) may be different based on properties of the first resin (e.g., base resin), the difference in the solubility parameter may be determined based on the properties of the first resin. The properties of the first resin may include, but is not limited to, a kind of the first resin, or a value of the solubility parameter of the first resin. In one embodiment, the difference in solubility parameter may be selected by considering immiscibility between the first resin and the second resin in a melting mixture of the first and second resins.

By way of an example, in the case that the resin blend of the first and second resins having the difference in solubility parameter of 0.001 to 10 $(J/cm^3)^{1/2}$ at 25° C. is used, when the resin blend is melt-processed, the melt-processed resin blend is exposed to an ambient air, the first and second resins can be separated due to the degree of immiscibility between the first resin and second resin. Particularly, the second resin having a difference in solubility parameter from the first resin at 25° C. of 0.001 to 10 $(J/cm^3)^{1/2}$ may be immiscible with the first resin. Thus, the second resin having additionally lower surface tension or lower melt viscosity than that of the first resin may move and be positioned adjacent to an ambient air to form a second resin layer. A first resin layer may be positioned on an inner side of the second layer. Accordingly, a layer separation can be occurred between the first and second resins of the resin blend.

In still another embodiment, a molecular weight distribution (PDI) of the second resin is 1 to 2.5 or 1 to 2.3. The molecular weight distribution can also be 1 to 2, 1.3 to 2.5, 1.5 to 2.5, or 1.3 to 2.3. The lower and/or upper limits of the molecular weight distribution (PDI) of the second resin may be any numeric value of 1 to 2.5. It will be apparent to one of skilled in the art that the listed ranges are only examples for the purpose of the description of the present invention and any value within the range of 1 to 2.5 can be selected. When the molecular weight distribution of the second resin is greater than 2.5, the first resin is easily mixed with the second resin due to the low molecular weight portion of the second resin, or the mobility of the second resin in a mixture of melting state is degraded due to the high molecular weight portion thereof, and thus the layer separation between the first resin and the second resin does not easily occur.

In still another embodiment, a weight average molecular weight (Mw) of the second resin of the resin blend is 30,000 to 200,000, or 50,000 to 150,000. The weight average molecular weight (Mw) of the second resin of the resin blend can also be 50,000 to 200,000, 80,000 to 200,000, 80,000 to 150,000, 50,000 to 120,000, or 80,000 to 120,000. The lower and/or upper limits of the weight average molecular weight (Mw) of the second resin may be any numeric value of 30,000 to 200,000. It will be apparent to one of skilled in the art that the listed ranges are only examples for the purpose of the description of the invention and any value within the range of 30,000 to 200,000 can be chosen. When the weight average molecular weight is smaller than 30,000, the first resin is easily mixed with the second resin, and when the weight average molecular weight is greater than 200,000, the mobility of the second resin in a mixture of melting state is degraded and thus the layer separation between the first and second resin does not easily occur.

Meanwhile, the first resin may determine the physical properties of a resin article and may be selected according to any kind of the desired resin article and processing conditions. As the first resin, a synthetic resin may be used without limitation, but may preferably include a styrene-based resin such as an acrylonitrile butadiene styrene (ABS)-based resin, a polystyrene-based resin, an acrylonitrile styrene acrylate (ASA)-based resin or a styrene-butadiene-styrene block copolymer-based resin; a polyolefin-based resin such as a high density polyethylene-based resin, a low density polyethylene-based resin or a polypropylene-based resin; a thermoplastic elastomer such as an ester-based thermoplastic elastomer or olefin-based thermoplastic elastomer; a polyoxyalkylene-based resin such as a polyoxymethylene-based resin or a polyoxyethylene-based resin; a polyester-based resin such as a polyethylene terephthalate-based resin or a polybutylene terephthalate-based resin; a polyvinylchloride-based resin; a polycarbonate-based resin; a polyphenylenesulfide-based resin; a vinyl alcohol-based resin; a polyamide-based resin; an acrylate-based resin; engineering plastics; or a copolymer or mixture thereof.

The engineering plastics are a group of plastics that exhibit superior mechanical and thermal properties. By way of examples, polyetherketone, polysulphone, polyimides and the like may be used as the engineering plastics.

The second resin shows the difference in physical properties from the first resin as described above, and may be chosen to provide specific functions to a surface of a resin article. The functions of the second resins are not particularly limited. For example, the second resins may be resins providing a high surface hardness function, an anti-wear function, an anti-contamination function, an anti-fingerprint function, a color, a pearling function, a high-gloss function, a non-gloss function, a barrier function or a combination thereof.

The second resin may include a resin to which a fluorine or fluorine-substituted organic functional group is introduced. When the fluorine or fluorine-substituted organic functional group is introduced, the surface energy or melt viscosity of the second resin is decreased. As a result, the second resin in a mixture of melting state may more easily move to contact with an ambient air, and the above-described layer separation in the process such as extrusion or injection may more easily occur. As the surface energy of the second resin is decreased due to the fluorine or fluorine-substituted organic functional group, the surface of the resin article may have a lower adhesive strength with respect to an organic or inorganic material, thereby obtaining excellent contamination resistance.

As an example of the fluorine-substituted organic functional group, a fluorine-substituted alkyl group having 1 to 30 carbon atoms; or a fluorine-substituted hydroxyalkyl group having 1 to 30 carbon atoms may be included, and at least one or two thereof may be introduced to the resin.

More specifically, the fluorine-substituted organic functional group may include an alkyl group having 1 to 30 carbon atoms with which at least three fluorine atoms are substituted, or an alkyl or hydroxyalkyl group having 1 to 10 carbon atoms including a perfluoroalkyl group having 1 to 10 carbon atoms.

Examples of the fluorine-substituted organic functional groups may include a trifluoromethyl group, a trifluoroethyl group, a trifluoropropyl group, a perfluorohexyl ethyl group, a pentafluoropropyl group, a perfluorobutyl ethyl group, a perfluorobutyl hydroxypropyl group, a perfluorohexyl hydroxypropyl group, a perfluoromethylbutyl hydroxypropyl group, a perfluorodecyl ethyl group, a tetrafluoropropyl group, an octafluoropentyl group, a dodecafluoroheptyl group and a hexafluorobutyl group. Examples of the resin which may be included in the second resin may include a (meth)acrylate-based resin, an epoxy-based resin, an oxetane-based resin, an isocyanate-based resin, a silicon-based rein, and a copolymer or mixture thereof.

The (meth)acrylate-based resin is a resin formed by polymerizing an acryl or methacryl monomer as a main component, which may include, but is not limited to, alkyl methacrylates such as methyl methacrylate, ethyl methacrylate, propyl methacrylate, butyl methacrylate, cyclohexyl methacrylate, octyl methacrylate, lauryl methacrylate or stearyl methacrylate; alkyl acrylates such as methyl acrylate, ethyl acrylate, propyl acrylate, butyl acrylate, octyl acrylate, lauryl acrylate or stearyl acrylate; or glycidyl(meth)acrylates such as glycidyl methacrylate or glycidyl acrylate.

The epoxy-based resin is a resin containing an epoxy group, and may be, but is not limited to, a bisphenol type such as bisphenol A, bisphenol F, bisphenol S or a hydro additive thereof; a novolac type such as phenol novolac or cresol novolac; a nitrogen-containing ring type such as triglycidyl isocyanurate or hydantoin; an alicyclic type; an aliphatic type; an aromatic type such as naphthalene or biphenyl; a glycidyl type such as glycidyl ether, glycidyl amine or glycidyl ester; a dicyclo type such as dicyclopentadiene; an ester type; or an ether ester type.

The oxetane-based resin is a resin formed by polymerizing an oxetane monomer having at least one oxetane ring, and may be, but is not limited to, 1,4-bis[(3-ethyl-3-oxetanyl-methoxy)methyl]benzene, di[1-ethyl(3-oxetanyl)]methylether, or a polyoxetane compound such as phenol novolac oxetane, terephthalate bisoxetane or biphenylene bisoxetane.

The isocyanate-based resin is a resin containing an isocyanate group, and may be, but is not limited to, diphenylmethane diisocyanate (MDI), toluene diisocyanate (TDI) or isophorone diisocyanate (IPDI).

The silicon-based resin is a resin containing a main chain connected by a siloxane bond which is a silicon-oxygen bond, and may be, but is not limited to, polydimethylsiloxane (PDMS).

The second resin may have a thermal curable functional group and/or a radiation, such as UV, curable functional group without specific limitation. When a thermal curable functional group is included in the second resin, hardness may be increased due to the crosslinks formed in melting process.

The resin blend may include the second resin in an amount of 0.1 to 50 parts by weight, or 1 to 20 parts by weight, based on 100 parts by weight of the first resin. The amount of second resin may also be 0.1 to 35 parts by weight, 0.1 to 20 parts by weight, 5 to 50 parts by weight, 10 to 50 parts by weight, 5 to 35 parts by weight or 5 to 20 parts by weight, based on 100 parts by weight of the first resin. The lower and/or upper limits of the amount of the second resin included in the resin blend, may be any numeric value of 0.1 to 50 parts by weight based on 100 parts by weight of the first resin. It will be apparent to one of skilled in the art that the listed ranges are only examples for the purpose of the description of the present invention and any value within the range of 0.1 to 50 parts by weight can be chosen. When the second resin is included in an amount smaller than 0.1 parts by weight based on 100 parts by weight of the first resin, the layer separation does not occur. When the second resin is included in an amount greater than 50 parts by weight, the manufacturing cost of the resin article increases due to the high cost of the second resin.

In another embodiment, a resin blend for forming a layer-separated structure includes a base resin and a functional resin. A value of a surface energy of the functional resin is different from that of the base resin, and the value of the surface energy of the functional resin is dependent on properties of the base resin.

The base resin, for example, a first resin, may substantially determine the physical properties of a resin article. The functional resin, for example, a second resin, may provide specific functions to a surface of a resin article. The properties of the base resin and the specific functions of the second resin are the same as described the above.

Figure 6:
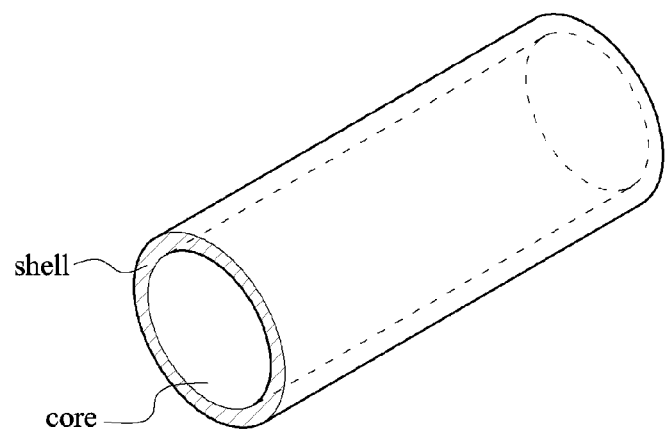
FIG. 6 is an illustrative schematic diagram showing a pellet having a core and a shell.

The present invention further provides a pellet prepared using the resin blend described above. The pellet may have a core having a first resin and a shell having a second resin formed on a surface of the pellet by layer separation. The first resin is disposed in the middle thereof (core), and a second resin is layer-separated from the first resin and disposed to surround the first resin and to form a shell of the pellet. The structure of a pellet can be illustrated as shown in FIG. 6.

The first resin and the second resin have different properties as described above. For example, the second resin may include a resin to which a fluorine or fluorine-substituted organic functional group is introduced. Also, the first resin and the second resin may have a difference in surface energy from the first resin at 25° C. of 0.1 to 35 mN/m; a difference in melt viscosity of 0.1 to 3000 pa*s at a shear rate of 100 to 1000 $s^{-1}$ and at a processing temperature of the pellet; or a difference in solubility parameter of 0.001 to 10.0 $(J/cm^3)^{1/2}$ at 25° C. Further, the second resin may have a molecular weight distribution (PDI) of 1 to 2.5 or a weight average molecular weight (Mw) of 30,000 to 200,000. The first and second resins have already been described in detail, and thus further detailed description will be omitted.

The present invention still further provides a method of preparing a resin article comprising a melt processing of the resin blend as described above. The resin article prepared has a layer-separated structure. In one embodiment, the method includes melting a blend of first and second resins to form a melt blend and processing the melt blend to prepare a resin article. The second resin includes a resin to which a fluorine or fluorine-substituted organic functional group is introduced. The surface energy difference between the first resin and the second resin is 0.1 to 35 mN/m at 25° C.

As described above, since the second resin has a different physical property from the first resin such as higher hydrophobicity, the layer separation may occur during the melt processing such as injection or extrusion of the resin blend. This layer separation enables a layer of the second resin to be formed on a surface of pellets or a resin article without the need of additional process and thus provides the same results as applying a coating on a surface of pellets or a resin article by a separate step. Further, since the second resin can be formed to have a function such as gloss or anti-contamination and can be separated from the first resin during the melt processing of the resin blend, the resin article in which the first resin constitutes a body and the second resin forms a surface on the body can be easily manufactured without performing additional process. Still further, when the first and second resins are used to form a pellet, the pellet having a core of the first resin and a shell of the second resin can be manufactured by the melt processing of the resin blend without performing any additional process.

Particularly, the second resin may include a resin to which a fluorine or fluorine-substituted organic functional group is introduced, and the fluorine or fluorine-substituted organic functional group can reduce a surface energy or melt viscosity of the second resin, thereby having high hydrophobicity during the melting process such as extrusion or injection. Accordingly, the second resin in a mixture of melting state may more easily move to contact with an ambient air and a resin article having improved mechanical and surface characteristics may be provided since the second resin is disposed on a surface of the resin article. In addition, since the fluorine or fluorine-substituted organic functional group may reduce the surface energy of the second resin, the surface of the resin article may have a lower adhesive strength with respect to an organic or inorganic material, and have excellent contamination resistance.

Furthermore, the melt processing may be performed under a shear stress, and may include, but is not limited to, injection and extrusion.

In one embodiment, the resin blend may be prepared to include a first resin and a second resin that have a difference in physical properties, for example, surface energy, melt viscosity or solubility parameter. The resin blend may be melted to form a melt blend and the melt blend may be further processed to form pellets or a resin article. For example, the melted resin blend may be subject to an extrusion process to prepare a pellet. As described above, the first and second resins may be separated during the melt processing such as extrusion. Particularly, the second resin may move to contact with an ambient air due to its hydrophobic property compared to the first resin. A second resin layer may be positioned adjacent to an ambient air, and a layer substantially formed of a first resin layer may be positioned on an opposite side to the ambient air but disposed adjacent to the second resin layer. Accordingly, the resin article may have a body that is formed of the first resin and a surface that is on the body and is formed of the second resin. Further, by the above described process, the pellet may have structure in which the first resin is disposed in the middle of the pellet and the second resin is disposed to surround the first resin.

In another embodiment, the pellet may be further processed, for example injection, to form a resin article. For example, the pellet having first and second resins of different physical properties may be melted and further processed, for example, injected, to form a final product, for example, a resin article. As described above, due to the difference in various physical properties, for example, surface energy, melt viscosity or solubility parameter, of the first and second resins of the pellets, the resin article formed of using pellets may have separated layers, i.e., a body formed of the first resin and a surface layer formed of the second resin and placed on the body. Although it is illustrated that the pellets of core-shell structure having the first and second resins are melt-processed to form a resin article for the purpose of explanation, it will be apparent to one of skilled in the art that a mixture of two or more pellets or pellets including the composition of two or more resins may be used to form a resin article. Alternatively, the resin blend may be directly prepared into a resin article through the melt processing such as injection, as described above. The processing temperature to be applied may be changed depend on kinds of the first and second resins used in the melt processing of the resin blend.

In some embodiments, the method of preparing a resin article may further include curing a product having a layer-separated structure (for example, a resin article having a body and a surface layer on the body) obtained from the melt processing of the resin blend. For example, after an extrusion or injection, thermal curing and/or radiation curing, such as UV curing, may be further performed on the melt-processed product. When necessary, chemical or physical treatment, such as a heat treatment, may be performed after the process.

Meanwhile, the method of preparing a resin article may further include preparing a second resin before the melt processing of the resin blend. The second resin may be selected depending on a first resin, as described above. For example, the second resin may be selected such that a value of a surface energy of the second resin is less than that of the first resin. Further, the second resin may be selected to add specific functions on a surface of the resin article. As examples for the preparation of the second resin, there is bulk polymerization, solution polymerization, suspension polymerization, or emulsion polymerization.

In the suspension polymerization method, the second resin may be prepared by dispersing a monomer in a reaction medium, adding and blending an additive such as a chain transfer agent, an initiator and a dispersion stabilizer in the reaction solvent and polymerizing the blend at 40° C. or higher. One of skilled in the art can easily select the kind of monomer based on a desired function such as an abrasion resistance function, an anti-wear function, an anti-contamination function, an anti-fingerprint function, a colored function, a pearl function, a high-gloss function, a non-gloss function and a barrier function. By way of examples of the monomer, there are (meth)acrylate monomers, epoxy monomers, oxetane monomers, isocyanate monomers, silicon monomers, fluorine-based monomers or a copolymer thereof.

The reaction medium may be any medium known to be conventionally used to prepare a synthetic resin, polymer or copolymer without limitation. For example, the reaction medium may be distilled water. The chain transfer agent which can be added to the reaction solvent may be, but is not limited to, an alkyl or aryl mercaptan such as n-butyl mercaptan, n-dodecyl mercaptan, tertiary dodecyl mercaptan, isopropyl mercaptan or aryl mercaptan; a halogen compound such as ketone tetrachloride; or an aromatic compound such as an alpha-methylstyrene dimer or an alpha-ethylstyrene dimer. The initiator is a polymerization initiator, which may be, but is not limited to, a peroxide such as octanoyl peroxide, decanoyl peroxide or lauroyl peroxide, or an azo-based compound such as azobisisobutyronitrile or azobis-(2,4-dimethyl)-valeronitrile. The dispersion stabilizer which can be included in the reaction medium may be, but is not limited to, an organic distribution agent such as polyvinyl alcohol, polyolefin-maleic acid or cellulose, or an inorganic distribution agent such as tricalcium phosphate.

The first and second resins have already been described above in detail, and thus further description thereof will be omitted.

The present invention still further provides a resin article having a layer-separated structure.

In one embodiment, the resin article having a layer-separated structure includes a first resin layer; a second resin layer formed on the first resin layer; and an interface layer formed between the first resin layer and the second resin layer. Here, the interface layer includes a first resin and a second resin. Also, the second resin layer includes a resin to which a fluorine or fluorine-substituted organic functional group is introduced. Such a structural characteristic of the resin article including a layer-separated structure is attributed to using a resin blend comprising specific first and second resins.

The specific first and second resins may be a resin which has certain physical properties and/or a certain molecular weight distribution and/or a certain weight average molecular weight. For example, the physical properties may include a surface energy, a melt viscosity or a solubility parameter. Since the resin article has such a structural characteristic, the resin article may have improved mechanical and surface characteristics. Further, since coating or plating is not required for manufacturing the resin article, a manufacturing time and/or cost can be reduced, and productivity can be increased.

The resin article is formed in such a structure that the first resin layer is separated from the second resin layer by an interface layer and the second resin layer is exposed to an ambient air, which is a novel structure that has not been known in the art. This structure may not be formed by extrusion and injection process of a general resin, and thus it is difficult to obtain the effects resulting from this novel structure.

The first resin layer may refer to a part substantially comprising the first resin and disposed inner side of the resin article due to low hydrophobicity. The second resin layer may refer to a part substantially comprising the second resin and disposed on the surface of the resin article due to high hydrophobicity, which provides an improved surface hardness or excellent anti-contamination characteristic to the surface of the resin article.

Meanwhile, the resin article may include an interface layer comprising a first resin and a second resin and formed between the first resin layer and the second resin layer. The interface layer may serve as a boundary formed between the layer-separated first and second resin layers, and include the first and second resins. In the interface layer, the first resin is physically or chemically bound to the second resin, and the first resin layer may be bound to the second resin layer by the interface layer.

As described above, the resin article may have such a structure in which the first resin layer is separated from the second resin layer by the interface layer, and the second resin layer is exposed to an ambient air. For example, the resin article may have a structure in which the first resin layer, an interface layer and a second resin layer are sequentially stacked, or a structure in which the first resin layer is disposed, and the interface layers and the second resin layer are disposed above and below the first resin layer. Alternatively, the resin article may have such a structure that the first resin layer formed in various three-dimensional shapes, for example, spherical, circular, polyhedral and sheet-type shapes, is sequentially surrounded by the interface and the second resin layer.

Meanwhile, the first resin layer, the second resin layer and the interface layer may be observed using a scanning electron microscope (SEM) after a sample goes through a low temperature impact test and a cross-section of the sample is etched using a THF vapor. To observe the first and second resin layers and the interface layer and measure a thickness of each layer, a sample was cut with a diamond knife using a microtoming device to obtain a smooth cross-section, and the smooth cross-section was etched using a solution capable of more selectively dissolving a second resin than a first resin. The etched cross-section is dissolved to different levels of depth according to contents of the first and second resins, and when the cross-section is viewed at a 45-degree angle from a surface thereof through SEM, the first resin layer, the second resin layer and the interface layer may be observed due to a shade difference and thicknesses thereof may be measured. In the present invention, as the solution more selectively dissolving the second resin, a 1,2-dichloroethane solution (10 volume %, in EtOH) is used, but is merely an example. Therefore, any solution having a higher solubility of the second resin than the first resin may be used without limitation, and the solution may vary according to the kind and composition of the second resin. The thickness of the interface layer may be 0.01 to 95% or 0.1 to 70%, of the total thickness of the second resin layer and the interface layer. When the thickness of the interface layer is 0.01 to 95% to the total thickness of the second resin layer and the interface layer, the interface adhesive strength of the first and second resin layers is excellent. Thus, the first and the second resin layers are not detached, and the surface characteristic attributed to the second resin layer may be considerably improved. On the other hand, when the thickness of the interface layer is too smaller than the total thickness of the second resin layer and the interface layer, the adhesive strength between the first and second resin layers is decreased, and thus both layers may be detached. However, when the thickness of the interface layer is too thick compared to the total thickness of the second resin layer and the interface layer, the improvement in a surface characteristic of the second resin layer may be insignificant.

The second resin layer may have a thickness of 0.01 to 60%, 0.1 to 40% or 1 to 20%, of the total thickness of the resin article. As the second resin layer has a thickness in a specific range, it can provide the surface of the resin article with specific functions. Here, when the second resin layer is too thin, it may be difficult to sufficiently improve the surface characteristic of the resin article, and when the second resin layer is too thick, the mechanical property of the second resin may be reflected to the resin article, and thus the mechanical property of the first resin may be changed.

The first and second resins have already been described above in detail, and thus further description thereof will be omitted.

In another embodiment, a melt-processed resin article that includes a first resin layer; and a second resin layer formed on the first resin layer. Here, the component of the first resin layer is detected on a surface of the second resin layer by an infrared (IR) spectrometer. Also, the second resin layer includes a resin to which a fluorine or fluorine-substituted organic functional group is introduced.

A structure of the resin article, that is, a structure in which the component of the first resin layer is detected from the surface of the second resin layer by the IR spectrometer, is novel, and has not been known in the art. Generally, in the case of a second layer applied by a coating process, the component of the first resin layer is difficult to be detected from the surface of the second resin layer.

The surface of the second resin layer refers to a surface exposed to the ambient air, not to the first resin layer.

In addition, the component of the first resin layer refers to at least one of the components included in the first resin layer.

The first and second resins have already been described above in detail, and thus further description thereof will be omitted.

In addition, another embodiment of the present invention provides an automobile part, a helmet, a part of electric device, a part of sewing machine, toys or pipes that contain a melt-processed resin article described above.

The present invention will be described with reference to the following Examples in detail. However, the present invention is not limited to the following Examples.

Measurement of Surface Energy

According to the Owens-Wendt-Rabel-Kaelble (OWRK) method, surface energies of first resins and second resins were measured using a drop shape analyzer (Kruss, DSA100). More specifically, the first resins and second resins were dissolved in a methyl ethyl ketone solvent to have a concentration of 15 wt %, and then coated on a LCD glass by bar coating. The coated LCD glass was pre-dried in an oven at 60° C. for 2 minutes and then dried at 90° C. for 1 minute. After drying (or curing), deionized water and diiodomethane were dropped 10 times on the coated surface at 25° C., respectively, to get an average value of a contact angle, and surface energy was calculated by substituting a numerical value into the OWRK method.

Measurement of Melt Viscosity

Melt viscosities of first resins and second resins were measured using a Capillary Rheometer 1501 (Gottfert). More specifically, after a capillary die was attached to a barrel, the first resins and second resins were put into the barrel by dividing to 3 parts. A shear viscosity (pa*s) according to a shear rate of 100 to 1000 s$^{-1}$ was measured at a processing temperature of 240° C.

Measurement of Solubility Parameter

While there are some methods of measuring and calculating solubility parameters, the solubility parameters of first resins and second resins were calculated at 25° C. using a known method, the Van Krevelen method [refer to Bicerano, J., Prediction of Polymer Properties, third edition, Marcel Dekker Inc., New York (2002), the disclosure of which is incorporated herein by reference in its entirety]. According to the Van Krevelen method, the solubility parameter was calculated using a group contribution theory, and defined as the following formula:

$$\delta \text{ (solubility parameter)} = \sqrt{e_{coh}} = \sqrt{\frac{E_{coh}}{V}}$$

In the formula, $E_{coh}$ is a cohesive energy, V is a molar volume, and $e_{coh}$ is a cohesive energy density. The cohesive energy ($E_{coh}$) is defined as follows:

$$E_{coh} = 10570.9 \times (^0X^v - ^0X) + 9072.8 \times (2 \times ^1X - ^1X^v) + 1018.2 \times N_{VKH}$$

In the formula, $^0X$, $^1X$, $^0X^v$ and $^1X^v$ are connectivity indices, and $N_{VKH}$ is a correlation term. Each variant was calculated with reference to the disclosed literature [Bicerano, J., Prediction of Polymer Properties, third edition, Marcel Dekker Inc., New York (2002)].

Observation of Feature of Cross-Section

Samples went through a low temperature impact test. Then, fracture surfaces of the samples were etched using THF vapor, and a layer-separated cross-section was observed using an SEM.

Meanwhile, to measure thicknesses of layer-separated first and second resin layers and an interface layer, the samples of the following Examples and Comparative Examples were cut with a diamond knife at −120° C. using a microtoming device (Leica EM FC6), thereby obtaining a smooth cross-section. The part of the sample with the microtomed smooth cross-section was dipped in a 1,2-dichloroethane solution (10 volume %, in EtOH) to etch for 10 seconds, and then washed with distilled water. The etched cross-sectional part was dissolved to different levels of depth according to the contents of the first and second resins, and could be observed using an SEM. That is, when the cross-section was viewed at a 45-degree angle from a surface, due to a shade difference, the first resin layer, the second resin layer and the interface layer could be observed, and a thickness of each layer could be measured.

Experiment for Measuring Pencil Hardness

Pencil hardness of samples was measured under a constant load of 500 g using a pencil hardness tester (Chungbuk Tech). Scratches were made on a surface of the samples by standard pencils (Mitsubishi; grade 6B to 9H) with a fixed angle of 45 degrees, and therefore a change rate of the surface was observed (ASTM 3363). The values of pencil hardness are average values of the results obtained from tests performed 5 times.

Measurement of Molecular Weight Distribution (PDI)

Molecular weight distribution was measured using gel permeation chromatography (GPC) under conditions as follows:

Instrument: 1200 series produced by Agilent Technologies

Column: 2 PLgel mixed Bs produced by Polymer Laboratories

Solvent: THF

Column Temperature: 40° C.

Concentration of Sample: 1 mg/mL, 100 L injection

Standard: Polystyrene (Mp: 3900000, 723000, 316500, 52200, 31400, 7200, 3940 or 485)

As an analysis program, ChemStataion provided by Agilent Technologies was used, and a weight average molecular weight (Mw) and a number average molecular weight (Mn) were measured using gel permeation chromatography (GPC), and the molecular weight distribution was then calculated from an equation of Mw/Mn.

Test for Measuring Contamination Resistance

Contamination Resistance of samples was measured. Specifically, the sample was dissolved to 15 wt % in a methyl ethyl ketone solvent, and coated on an LCD glass by bar coating. Subsequently, the coated LCD glass was pre-dried in an oven at 60° C. for 2 minutes, and dried in an oven at 90° C. for 1 minute.

Subsequently, after writing on a surface of the dried sample with a pen (Name Pen, Monami), two lines having a length of approximately 5 cm were drawn and wiped out with a superfine fiber unwoven fabric to observe a mark of the pen with the naked eye. When the mark of the pen was completely removed, the above-described procedure was repeated and continued until the mark of the pen was not removed. A total number of the repeated procedures was recorded.

Surface Analysis by IR Spectrometer

The experiment was performed using a UMA-600 IR microscope equipped with a Varian FTS-7000 spectrometer (Varian, USA) and a mercury cadmium telluride (MCT) detector, and detection of spectra and data processing were performed using Win-IR PRO 3.4 software (Varian, USA). Conditions of the experiment were as follows:

Germanium (Ge) ATR crystal having refractive index of 4.0

Spectral Resolution of Middle Infrared Spectrum obtained by Attenuated Total Reflection: 8 cm-1 and Range of 16 Scans: 4000 cm-1-600 cm-1.

Internal Reference Band: Carbonyl Group (C=O str., ~1725 cm-1) of Acrylate

Original Component of First Resin: Butadiene Compound [C=C str. (~1630 cm-1) or =C—H out-of-plane vib. (~970 cm-1)]

Peak intensity ratios [IBD(C=C)/IA(C=O)] and [IBD(out-of-plane)/IA(C=O)] were calculated, and the detection of spectra was performed 5 times in different regions of one sample, and an average value and a standard deviation were calculated.

EXAMPLE 1

(1) Preparation of First Resin and Second Resin

As a first resin, a first resin-1 (a thermoplastic resin composed of 60 wt % methyl methacrylate, 7 wt % acrylonitrile, 10 wt % butadiene and 23 wt % styrene) was used. As a second resin, a second resin-1 was prepared as following: 1500 g of distilled water and 4 g of 2% polyvinylalcohol aqueous solution as a dispersing agent were put into a 3-liter reactor and dissolved. Subsequently, 760 g of methyl methacrylate, 40 g of perfluorohexylethyl methacrylate, 2.4 g of n-dodecyl mercaptan as a chain transfer agent and 2.4 g of azobis-(2,4-dimethyl)-valeronitrile as an initiator were further added thereto, and mixed while stirring at 400 rpm. The mixture was polymerized by 3-hour reaction at 60° C., and cooled to 30° C., thereby obtaining a bead-type second resin-1. Afterward, the second resin-1 was washed three times with distilled water, dehydrated and dried in an oven.

As the results of measurement of the physical properties of the first resin-1 and the second resin-1, it was shown that a difference in surface energy was 5.4 mN/m, a difference in melt viscosity was 250 pa*s, a difference in solubility parameter was 0.2 (J/cm3)½, a weight average molecular weight of the second resin obtained by GPC was 100K, and a molecular weight distribution (PDI) of the second resin was 2.

(2) Preparation of Resin Blend and Resin Article Using the Same

Figure 8:
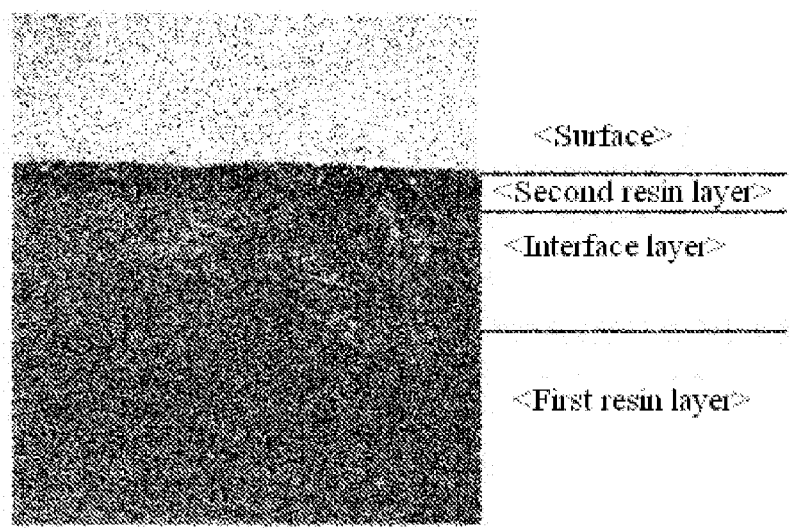
FIG. 8 is a SEM image illustrating a cross-sectional view of a resin article treated with a solution capable of selectively dissolving a second resin, when viewed at a 45-degree angle from the surface prepared according to Example 1.

After 90 parts by weight of the first resin-1 was blended with 10 parts by weight of the second resin-1, the blend was extruded using a twin-screw extruder (Leistritz) at 240° C., thereby obtaining a pellet. A layer separation was observed in the pellet. Then, the pellet was injected using an EC100Φ30 injector (ENGEL) at 240° C., thereby obtaining a sample 1 having a thickness of 3200 μm. A thickness of the second resin layer was 102 μm and a thickness of an interface layer was 15 μm. In addition, an angle of contact was 75 degrees, a pencil hardness of the sample 1 was 2H, and layer separation occurred. The feature of the cross-section of the sample 1 observed at a 45-degree angle from the surface is shown in FIG. 8. In evaluation of contamination resistance, a number of repetitions of the test performed until a mark was no longer removed was 40. The peak intensity ratio [IBD(C=C)/IA(C=O)] measured by an IR spectrometer was averagely 0.0113 with a standard deviation of 0.0002, and the peak intensity ratio [IBD(out-of-plane)/IA(C=O)] was averagely 0.398 with a standard deviation of 0.0021.

EXAMPLE 2

(1) Preparation of First Resin and Second Resin

As a first resin, the first resin-1 of Example 1 was used. As a second resin, a second resin-2 was prepared by the same method as described in Example 1, except that 552 g of methyl methacrylate, 240 g of 3-ethyl-3-methacryloyloxymethyloxetane and 8 g of perfluorohexylethyl methacrylate were used instead of 760 g of methyl methacrylate and 40 g of perfluorohexylethyl methacrylate.

As the results of measurement of the physical properties of the first resin-1 and the second resin-2, it was shown that a difference in surface energy was 11.9 mN/m, a difference in melt viscosity was 280 pa*s, a difference in solubility parameter was 0.5 (J/cm3)½, a weight average molecular weight of the second resin obtained by GPC was 100K, and a molecular weight distribution (PDI) of the second resin was 2.1.

(2) Preparation of Resin Blend and Resin Article Using the Same

Figure 7:
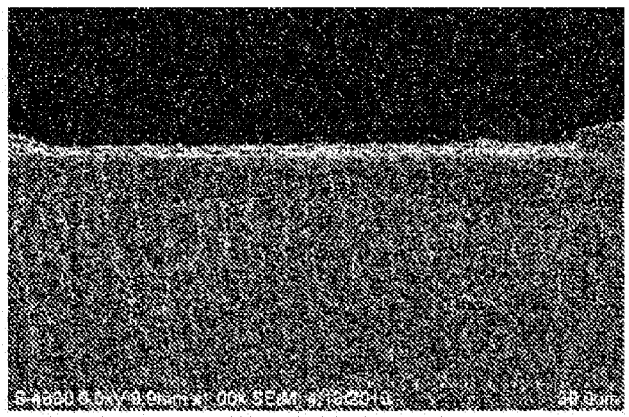
FIG. 7 is a SEM image illustrating a cross-sectional view of a resin article prepared according to Example 2.

A sample 2 having a thickness of 3200 μm was prepared by the same method as Example 1, except that 10 parts by weight of the second resin-2 was used instead of 10 parts by weight of the second resin-1. A thickness of the second resin layer was 14 μm and a thickness of an interface layer was 13 μm. In addition, an angle of contact was 82 degrees, a pencil hardness of the sample 2 was 2H, and layer separation occurred. The feature of the cross-section of the sample 2 observed by using SEM is shown in FIG. 7. In evaluation of contamination resistance, a number of repetitions of the test performed until a mark was no longer removed was 21.

EXAMPLE 3

(1) Preparation of First Resin and Second Resin

As a first resin, the first resin-1 of Example 1 was used. As a second resin, a second resin-3 was prepared by the same method as described in Example 1, except that 760 g of methyl methacrylate and 40 g of perfluorodecyl methacrylate were used instead of 760 g of methyl methacrylate and 40 g of perfluorohexylethyl methacrylate.

As the results of measurement of the physical properties of the first resin-1 and the second resin-3, it was shown that a difference in surface energy was 7.3 mN/m, a difference in melt viscosity was 260 pa*s, a difference in solubility parameter was 0.2 (J/cm3)½, a weight average molecular weight of the second resin obtained by GPC was 100K, and a molecular weight distribution (PDI) of the second resin was 2.

(2) Preparation of Resin Blend and Resin Article Using the Same

A sample 3 having a thickness of 3200 μm was prepared by the same method as Example 1, except that 10 parts by weight of the second resin-3 was used instead of 10 parts by weight of the second resin-1. A thickness of the second resin layer was 50 μm and a thickness of an interface layer was 21 μm. In addition, an angle of contact was 83 degrees, a pencil hardness of the sample 3 was 1.5H, and layer separation occurred. In evaluation of contamination resistance, a number of repetitions of the test performed until a mark was no longer removed was 15.

EXAMPLE 4

(1) Preparation of First Resin and Second Resin

As a first resin, the first resin-1 of Example 1 was used. As a second resin, a second resin-4 was prepared by the same method as described in Example 1, except that 680 g of methyl methacrylate and 120 g of perfluorohexylethyl methacrylate were used instead of 760 g of methyl methacrylate and 40 g of perfluorohexylethyl methacrylate.

As the results of measurement of the physical properties of the first resin-1 and the second resin-4, it was shown that a difference in surface energy was 14.5 mN/m, a difference in melt viscosity was 310 pa*s, a difference in solubility parameter was 0.5 (J/cm3)½, a weight average molecular weight of the second resin obtained by GPC was 100K, and a molecular weight distribution (PDI) of the second resin was 2.1.

(2) Preparation of Resin Blend and Resin Article Using the Same

A sample 4 having a thickness of 3200 µm was prepared by the same method as Example 1, except that 10 parts by weight of the second resin-4 was used instead of 10 parts by weight of the second resin-1. A thickness of the second resin layer was 120 µm and a thickness of an interface layer was 40 µm. In addition, an angle of contact was 86 degrees, a pencil hardness of the sample 4 was 2.5H, and layer separation occurred. In evaluation of contamination resistance, a number of repetitions of the test performed until a mark was no longer removed was 50.

EXAMPLE 5

(1) Preparation of First Resin and Second Resin

As a first resin, the first resin-1 of Example 1 was used. As a second resin, a second resin-5 was prepared by the same method as described in Example 1, except that 520 g of methyl methacrylate, 240 g of 3-ethyl-3-methacryloyloxymethyloxetane and 40 g of perfluorohexylethyl methacrylate were used instead of 760 g of methyl methacrylate and 40 g of perfluorohexylethyl methacrylate.

As the results of measurement of the physical properties of the first resin-1 and the second resin-5, it was shown that a difference in surface energy was 15.1 mN/m, a difference in melt viscosity was 290 pa*s, a difference in solubility parameter was 0.6 (J/cm3)½, a weight average molecular weight of the second resin obtained by GPC was 100K, and a molecular weight distribution (PDI) of the second resin was 2.1.

(2) Preparation of Resin Blend and Resin Article Using the Same

A sample 5 having a thickness of 3200 µm was prepared by the same method as Example 1, except that 10 parts by weight of the second resin-5 was used instead of 10 parts by weight of the second resin-1. A thickness of the second resin layer was 125 µm and a thickness of an interface layer was 10 µm. In addition, an angle of contact was 88 degrees, a pencil hardness of the sample 5 was 2H, and layer separation occurred. In evaluation of contamination resistance, a number of repetitions of the test performed until a mark was no longer removed was 62.

EXAMPLE 6

(1) Preparation of First Resin and Second Resin

As a first resin, the first resin-1 of Example 1 was used. As a second resin, a second resin-6 was prepared by the same method as described in Example 1, except that 560 g of methyl methacrylate, 200 g of cyclohexyl methacrylate and 40 g of perfluorohexylethyl methacrylate were used instead of 760 g of methyl methacrylate and 40 g of perfluorohexylethyl methacrylate.

As the results of measurement of the physical properties of the first resin-1 and the second resin-6, it was shown that a difference in surface energy was 7.4 mN/m, a difference in melt viscosity was 410 pa*s, a difference in solubility parameter was 0.6 (J/cm3)½, a weight average molecular weight of the second resin obtained by GPC was 100K, and a molecular weight distribution (PDI) of the second resin was 2.

(2) Preparation of Resin Blend and Resin Article Using the Same

A sample 6 having a thickness of 3200 µm was prepared by the same method as Example 1, except that 10 parts by weight of the second resin-6 was used instead of 10 parts by weight of the second resin-1. A thickness of the second resin layer was 10 µm and a thickness of an interface layer was 22 µm. In addition, an angle of contact was 84 degrees, a pencil hardness of the sample 6 was 2H, and layer separation occurred. In evaluation of contamination resistance, a number of repetitions of the test performed until a mark was no longer removed was 30.

EXAMPLE 7

(1) Preparation of First Resin and Second Resin

As a first resin, the first resin-1 of Example 1 was used. As a second resin, a second resin-7 was prepared by the same method as described in Example 1, except that 380 g of methyl methacrylate, 380 g of cyclohexyl methacrylate and 40 g of perfluorohexylethyl methacrylate were used instead of 760 g of methyl methacrylate and 40 g of perfluorohexylethyl methacrylate.

As the results of measurement of the physical properties of the first resin-1 and the second resin-7, it was shown that a difference in surface energy was 5.5 mN/m, a difference in melt viscosity was 450 pa*s, a difference in solubility parameter was 0.8 (J/cm3)½, a weight average molecular weight of the second resin obtained by GPC was 100K, and a molecular weight distribution (PDI) of the second resin was 2.

(2) Preparation of Resin Blend and Resin Article Using the Same

A sample 7 having a thickness of 3200 µm was prepared by the same method as Example 1, except that 10 parts by weight of the second resin-7 was used instead of 10 parts by weight of the second resin-1. A thickness of the second resin layer was 45 µm and a thickness of an interface layer was 10 µm. In addition, an angle of contact was 83 degrees, a pencil hardness of the sample 7 was 2.5H, and layer separation occurred. In evaluation of contamination resistance, a number of repetitions of the test performed until a mark was no longer removed was 35.

COMPARATIVE EXAMPLE 1

(1) Preparation of First Resin and Second Resin

As a first resin, the first resin-1 of Example 1 was used. As a second resin, a second resin-8 was prepared by the same method as described in Example 1, except that 560 g of methyl methacrylate and 240 g of 3-ethyl-3-methacryloyloxymethyloxetane were used instead of 760 g of methyl methacrylate and 40 g of perfluorohexylethyl methacrylate.

As the results of measurement of the physical properties of the first resin-1 and the second resin-8, it was shown that a difference in surface energy was 1 mN/m, a difference in melt viscosity was 280 pa*s, a difference in solubility parameter was 0.5 (J/cm3)½, a weight average molecular weight of the second resin obtained by GPC was 100K, and a molecular weight distribution (PDI) of the second resin was 2.

(2) Preparation of Resin Blend and Resin Article Using the Same

A sample 8 having a thickness of 3200 µm was prepared by the same method as Example 1, except that 10 parts by weight of the second resin-8 was used instead of 10 parts by weight of the second resin-1. A thickness of the second resin layer was 80 µm and a thickness of an interface layer was 30 µm. In addition, an angle of contact was 68 degrees, a pencil hardness of the sample 8 was 2H, and layer separation occurred. In evaluation of contamination resistance, a mark was not completely removed in the first test.

COMPARATIVE EXAMPLE 2

(1) Preparation of First Resin and Second Resin

As a first resin, the first resin-1 of Example 1 was used. As a second resin, a second resin-9 was prepared by the same method as described in Example 1, except that 560 g of methyl methacrylate and 240 g of cylcohexyl methacrylate were used instead of 760 g of methyl methacrylate and 40 g of perfluorohexylethyl methacrylate.

As the results of measurement of the physical properties of the first resin-1 and the second resin-9, it was shown that a difference in surface energy was 1.4 mN/m, a difference in melt viscosity was 410 pa*s, a difference in solubility parameter was 0.6 (J/cm3)½, a weight average molecular weight of the second resin obtained by GPC was 100K, and a molecular weight distribution (PDI) of the second resin was 1.9.

(2) Preparation of Resin Blend and Resin Article Using the Same

A sample 9 having a thickness of 3200 μm was prepared by the same method as Example 1, except that 10 parts by weight of the second resin-9 was used instead of 10 parts by weight of the second resin-1. A thickness of the second resin layer was 76 μm and a thickness of an interface layer was 23 μm. In addition, an angle of contact was 74 degrees, a pencil hardness of the sample 9 was 2H, and layer separation occurred. In evaluation of contamination resistance, a mark was not completely removed in the first test.

COMPARATIVE EXAMPLE 3

Comparative Example 3 was prepared with only the first resin-1 of Example. Particularly, 100 parts by weight of the first resin-1 of Example 1 was extruded using a twin-screw extruder (Leistritz) at 240° C., thereby obtaining a pellet. Then, the pellet was injected using an EC100Φ30 injector (ENGEL) at 240° C., thereby obtaining a sample 10 having a thickness of 3200 μm.

As the results obtained by measuring physical properties of the sample 10, a surface energy was 43 mN/m, an angle of contact was 69 degrees, and a pencil hardness was F. In evaluation of contamination resistance, a mark was not completely removed in the first test.

COMPARATIVE EXAMPLE 4

(1) Preparation of First Resin and Second Resin

As a first resin, the first resin-1 of Example 1 was used. As a second resin, a second resin-10 was prepared by the same method as described in Example 1, except that 1.6 g of n-dodecyl mercaptan as a chain transfer agent and 0.9 g of azobis-(2,4-dimethyl)-valeronitrile as an initiator were used instead of 2.4 g of n-dodecyl mercaptan and 2.4 g of azobis-(2,4-dimethyl)-valeronitrile.

As the results of measurement of the physical properties of the first resin-1 and the second resin-10, it was shown that a difference in surface energy was 4 mN/m, a difference in melt viscosity was 400 pa*s, a difference in solubility parameter was 0.5 (J/cm3)½, a weight average molecular weight of the second resin obtained by GPC was 100K, and a molecular weight distribution (PDI) of the second resin was 3.2.

(2) Preparation of Resin Blend and Resin Article Using the Same

A sample 11 having a thickness of 3200 μm was prepared by the same method as Example 1, except that 10 parts by weight of the second resin-10 was used instead of 10 parts by weight of the second resin-1. An angle of contact was 72 degrees, a pencil hardness of the sample 11 was 0.5H, and layer separation did not occur. In evaluation of contamination resistance, a number of repetitions of the test performed until a mark was no longer removed was 3.

COMPARATIVE EXAMPLE 5

A hard coating layer was formed on the sample 10 of Comparative Example 3 by forming a layer by coating a hard coating solution prepared by the inventor including a multi-functional acrylate (17.5 wt % DPHA, 10 wt % PETA, 1.5 wt % perfluorohexylethyl methacrylate, 5 wt % urethane acrylate EB 1290 from SK cytech, 45 wt % methyl ethyl ketone, 20 wt % isopropyl alcohol and 1 wt % IRGACURE 184 as a UV initiator from Ciba) using a Mayer bar #9 and drying the coating at 60 to 90° C. for 4 minutes to form a coating film, and curing the coating film by UV irradiation with an intensity of 3000 mJ/cm2.

A pencil hardness of the hard coating layer was 3H, and in evaluation of the contamination resistance, a number of repetitions of the test until a pen was no longer removed was 50. In addition, average values and standard variations of peak intensity ratios [IBD(C=C)/IA(C=O)] and [IBD(out-of-plane)/IA(C=O)] detected by an IR spectrometer were 0, respectively.

While the invention has been shown and described with reference to certain exemplary embodiments thereof, it will be understood by those skilled in the art that various changes in form and details may be made therein without departing from the scope of the invention as defined by the appended claims.

What is claimed is:

1. A resin blend comprising:
a first resin; and
a second resin comprising a resin to which a fluorine or fluorine-substituted organic functional group is introduced and having a molecular weight distribution of 1 to 2.5 and a difference in surface energy from the first resin at 25° C. of 0.1 to 35 mN/m, wherein the second resin includes at least one resin selected from the group consisting of a (meth)acrylate-based resin, an epoxy-based resin, an oxetane-based resin, an isocyanate-based resin, a silicon-based resin and a copolymer thereof, and
wherein the resin blend is capable of forming a layer-separated structure during melt processing under shear stress.

2. The resin blend according to claim 1, wherein a difference in melt viscosity between the first resin and the second resin is 0.1 to 3000 pa*s at a shear rate of 100 to 1000 s$^{-1}$ and a processing temperature of the resin blend.

3. The resin blend according to claim 1, wherein a difference in solubility parameter between the first resin and the second resin at 25° C. is 0.001 to 10.0 $(J/cm^3)^{1/2}$.

4. The resin blend according to claim 1, wherein the second resin has a weight average molecular weight of 30,000 to 200,000.

5. The resin blend according to claim 1, wherein the fluorine-substituted organic functional group comprises at least one selected from the group consisting of a fluorine-substituted alkyl group having 1 to 30 carbon atoms and a fluorine-substituted hydroxyalkyl group having 1 to 30 carbon atoms.

6. The resin blend according to claim 1, wherein the first resin includes at least one selected from the group consisting of a styrene-based resin, a polyolefin-based resin, a thermoplastic elastomer, a polyoxyalkylene-based resin, a polyester-based resin, a polyvinyl chloride-based resin, a polycarbonate-based resin, a polyphenylene sulfide-based resin, a vinyl alcohol-based resin, an acrylate-based resin, engineering plastics and a copolymer thereof.

7. A method of preparing a resin article, comprising:
melting the resin blend of claim 1 to form a melt blend; and then
processing the melt blend to form a layer-separated structure.

8. The method according to claim 7, wherein the melting and processing are performed under a shear stress.

9. The method according to claim 7, further comprising:
curing the layer-separated structure.

10. The method according to claim 9, wherein the curing is a thermal curing or radiation curing.

11. The resin blend according to claim 1, wherein the second resin has a molecular weight distribution of 1 to 2.3.

12. The resin blend according to claim 1, wherein the second resin has a molecular weight distribution of 1.3 to 2.3.

13. A pellet having a layer-separated structure, comprising:
a core including a first resin; and
a shell including a second resin including a resin to which a fluorine or fluorine-substituted organic functional group is introduced and having a molecular weight distribution of 1 to 2.5 and a difference in surface energy from the first resin at 25° C. of 0.1 to 35 mN/m,
wherein the second resin includes at least one resin selected from the group consisting of a (meth)acrylate-based resin, an epoxy-based resin, an oxetane-based resin, an isocyanate-based resin, a silicon-based resin and a copolymer thereof.

14. A method of preparing a resin article, comprising:
melting a pellet of claim 13 to form a melt; and
processing the melt to form a layer-separated structure.

15. A resin article having a layer-separated structure in melt processing, comprising:
a first resin layer including a first resin;
a second resin layer including a second resin formed on the first resin layer; and
an interface layer including the first resin and the second resin and formed between the first resin layer and the second resin layer,
wherein the second resin includes a resin to which a fluorine or fluorine-substituted organic functional group is introduced and has a molecular weight distribution of 1 to 2.5 and a difference in surface energy from the first resin at 25° C. of 0.1 to 35 mN/m, and
wherein the second resin includes at least one resin selected from the group consisting of a (meth)acrylate-based resin, an epoxy-based resin, an oxetane-based resin, an isocyanate-based resin, a silicon-based resin and a copolymer thereof.

16. The resin article having a layer-separated structure in melt processing according to claim 15, wherein component of the first resin layer is detected on a surface of the second resin layer by infrared spectrometer.

* * * * *